United States Patent
Iorgulescu et al.

(10) Patent No.: US 11,571,259 B2
(45) Date of Patent: Feb. 7, 2023

(54) SYSTEMS AND METHODS FOR GUIDING AN INSTRUMENT USING HAPTIC OBJECT WITH COLLAPSING GEOMETRY

(71) Applicant: MAKO Surgical Corp., Fort Lauderdale, FL (US)

(72) Inventors: Radu Iorgulescu, Boca Raton, FL (US); Dennis Moses, Doral, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 586 days.

(21) Appl. No.: 16/594,310

(22) Filed: Oct. 7, 2019

(65) Prior Publication Data

US 2020/0030043 A1    Jan. 30, 2020

Related U.S. Application Data

(60) Continuation of application No. 15/074,827, filed on Mar. 18, 2016, now Pat. No. 10,441,364, which is a division of application No. 13/340,664, filed on Dec. 29, 2011, now Pat. No. 9,289,264.

(51) Int. Cl.
| | |
|---|---|
| *A61B 34/20* | (2016.01) |
| *A61B 34/30* | (2016.01) |
| *A61B 34/00* | (2016.01) |
| *A61B 17/17* | (2006.01) |

(52) U.S. Cl.
CPC ............. *A61B 34/20* (2016.02); *A61B 17/17* (2013.01); *A61B 34/30* (2016.02); *A61B 34/76* (2016.02)

(58) Field of Classification Search
CPC ............ A61B 34/20; A61B 2034/2046; A61B 2034/2065; A61B 2034/2068; A61B 2034/2074; A61B 34/30; A61B 34/76; A61B 17/17; A61B 17/1703; A61B 17/1707
USPC .............................. 606/1, 130; 600/424–427
See application file for complete search history.

(56) References Cited

U.S. PATENT DOCUMENTS

| | | | | |
|---|---|---|---|---|
| 5,564,437 | A * | 10/1996 | Bainville | G01B 11/02 600/587 |
| 6,405,072 | B1 | 6/2002 | Cosman | |
| 8,010,180 | B2 | 8/2011 | Quaid et al. | |
| 8,287,522 | B2 * | 10/2012 | Moses | A61B 17/1764 606/1 |
| 8,571,628 | B2 | 10/2013 | Kang et al. | |
| 9,002,426 | B2 | 4/2015 | Quaid et al. | |
| 9,125,669 | B2 | 9/2015 | Ranawat et al. | |
| 9,289,264 | B2 | 3/2016 | Iorgulescu et al. | |

(Continued)

OTHER PUBLICATIONS

Dr. Sanja Dogramadzi, Haptics for Tele-surgery, http://www.brl.ac.uk/researchthemes/medicalrobotics/hapticsfortelesurgery.aspx, Nov. 2, 2012.

*Primary Examiner* — Ahmed M Farah
(74) *Attorney, Agent, or Firm* — Foley & Lardner LLP

(57) ABSTRACT

A system includes a surgical device, an instrument coupled to the surgical device and defining an instrument axis, and a processor operatively coupled to the surgical device. The processor is configured to determine a current orientation angle of an instrument axis based on an orientation of a target axis, establish a virtual boundary, control the surgical device to apply a force to constrain the instrument axis within the virtual boundary, and collapse the virtual boundary as the instrument axis is brought into alignment with the target axis.

20 Claims, 9 Drawing Sheets

(56) References Cited

U.S. PATENT DOCUMENTS

| | | | |
|---|---|---|---|
| 9,639,156 B2* | 5/2017 | Iorgulescu | G06F 3/0482 |
| 9,655,683 B2 | 5/2017 | Iorgulescu et al. | |
| 10,010,377 B2 | 7/2018 | Iorgulescu et al. | |
| 2004/0024311 A1 | 2/2004 | Quaid, III | |
| 2006/0142657 A1* | 6/2006 | Quaid | A61B 17/1703 |
| | | | 600/424 |
| 2007/0270685 A1* | 11/2007 | Kang | A61B 34/10 |
| | | | 600/424 |
| 2010/0170362 A1 | 7/2010 | Bennett et al. | |
| 2012/0215096 A1 | 8/2012 | Gilboa | |

* cited by examiner

SYSTEMS AND METHODS FOR GUIDING AN INSTRUMENT USING HAPTIC OBJECT WITH COLLAPSING GEOMETRY

CROSS REFERENCE TO RELATED APPLICATIONS

This application is a continuation of U.S. application Ser. No. 15/074,827, filed Mar. 18, 2016, which is a divisional of U.S. application Ser. No. 13/340,664, filed Dec. 29, 2011, all of which are hereby incorporated by reference herein in their entireties.

TECHNICAL FIELD

The present disclosure relates generally to haptic guidance systems and, more particularly, to systems and methods for guiding a surgical instrument using a haptic object having a collapsible geometry.

BACKGROUND

Many surgical procedures require the use of specialized tools to perform surgical tasks with a high degree of accuracy and precision. In some cases, such surgical procedures require precise positioning and/or placement of the tool at or near a particular point within a patient's anatomy. For example, many orthopedic procedures rely on the accurate placement of pins, screws, guide and/or post holes, or other elements in a precise position and orientation with respect to an anatomical feature of the patient. In order to ensure that these elements are properly positioned and oriented, great care is required on the part of the surgeon to ensure that the surgical tool(s) (e.g., drill, saw, reamer, etc.) used to position these elements is precisely and accurately aligned with the anatomy of the patient. However, this can be particularly challenging without the use of a guide and even more challenging in minimally-invasive procedures where visibility at the surgical site is limited or, in some cases, nonexistent.

Early solutions for enhancing the accuracy and precision of the alignment of tools in a surgical environment involved the use of mechanical guide elements, such as jigs. These mechanical guides were typically placed and/or mounted in close proximity to the anatomy of the patient and provided a physical guide that maintained a desired position and orientation of the tool during its operation.

For example, some prosthetic implants used in knee joint replacement surgeries comprise projections, keels, and/or other mechanical elements that are configured to fit within corresponding holes or voids created in the bone to secure the implant to the bone. In order to ensure the accurate placement of these voids, a jig was often used to mechanically align a drill in a desired position and orientation with respect to the bone of a patient. During operation of the drill, the jig would maintain the desired orientation while the surgeon advanced the drill into to the bone until the desired depth was reached.

Although these guide jigs enhanced the accuracy and precision of the placement of voids within the bone, they needed to be physically installed in proximity to the bone during the surgical procedure. The accurate alignment and placement of these guides can take a considerable amount of time, which could prolong the surgical procedure. Furthermore, mechanical jigs and cutting guides are typically too large to fit within the relatively small spaces allowed for minimally-invasive procedures.

With the advent of computer-assisted surgery (CAS) systems, surgeons were no longer required to rely on mechanical jigs for precision positioning of surgical instruments. Specifically, many CAS systems include surgical navigation and tracking software that displays a graphical representation of the surgical site. Using the navigation and tracking features of the CAS system, the surgeon can view the location of a surgical instrument relative to the patient's anatomy. Using the graphical interface as a guide, the surgeon can manually navigate the surgical tool to a desired position within the surgical site.

More sophisticated CAS systems are configured for interactive coupling with the surgical tools. These CAS systems may be equipped with force feedback controls that provide the surgeon with haptic feedback when, for example, the surgical tool interacts with certain pre-established virtual boundaries. Such virtual boundaries may be established to constrain the surgical instrument from undesired interactions with certain areas of the patient's anatomy. By strategically arranging the virtual boundaries for the force feedback controls, users can create "virtual" guides that define the areas in which the tool can operate, as well as areas that prohibit tool operation. If a surgical procedure requires the drilling of a post hole in a patient's bone, a virtual boundary may be established to define the desired position, orientation, and size of the hole. The virtual boundary may constrain a surgical tool from operating outside of the established boundary.

Although existing virtual guide methods provide a solution for defining the areas of allowed operation (and corresponding areas of constrained operation) of a surgical instrument, they may still be inefficient. For example, conventional virtual guide methods do include a solution for aligning a surgical tool in a proper orientation prior to engagement with the patient's anatomy. As a result, in surgical procedures that require precision cuts having specific orientations (such as the drilling of post or guide holes within bone), the surgeon may be required to manually "search" for the appropriate orientation by using the tip of the surgical tool as an exploring device to first locate the engagement point at the surface of the patient's bone. Once the engagement point has been located, the surgeon then manually pivots the surgical tool to locate the appropriate orientation for advancing the tool to the target point. Not only is such a manual process frustrating to the surgeon, it may unnecessarily prolong the surgery, which can increase costs.

The presently disclosed systems and methods for guiding a surgical instrument to a target orientation and/or position are directed to overcoming one or more of the problems set forth above and/or other problems in the art.

SUMMARY

According to one aspect, the present disclosure is directed to a computer-implemented method for guiding an instrument. The method may comprise determining, by a processor associated with a computer, an orientation angle of an instrument axis relative to a target axis. The method may also comprise establishing, by the processor, a haptic force associated with the instrument based on the determined orientation angle of the instrument axis relative to the target axis. The haptic force may be configured to constrain the instrument axis from being moved to an angle substantially greater than the orientation angle.

In accordance with another aspect, the present disclosure is directed to a method for guiding an instrument, comprising establishing, by a processor associated with a computer, a target axis. The method may also comprise determining, by the processor, a current orientation angle of the instrument relative to the target axis. The current orientation angle may be compared with a previous orientation angle relative to the target axis. If the current orientation angle is less than the previous orientation angle, a virtual haptic surface may be established relative to the target axis. The established virtual haptic surface may comprise a surface angle less than the previous orientation angle.

According to another aspect, the present disclosure is directed to an alternative method for guiding an instrument, comprising establishing a target axis that comprises a target point. The method may also comprise defining a virtual haptic volume based, at least in part, on the target point and the target axis. The method may further comprise determining a position of a reference point of the instrument. Upon determining that the position of the instrument reference point is within the virtual haptic volume, the virtual haptic volume may be decreased based on a detection of a corresponding decrease in an orientation angle of the instrument axis relative to the target axis.

In accordance with yet another aspect, the present disclosure is directed to a computer-assisted surgery system comprising a surgical device for performing at least one task associated with a surgical procedure and a processor, operatively coupled to the surgical device. The processor may be configured to determine an orientation angle of an instrument axis relative to a target axis. The processor may also be configured to apply a haptic force to the surgical device based on the determined orientation angle of the instrument axis relative to the target axis. The haptic force may be configured to constrain the instrument axis from being moved to an angle substantially greater than the orientation angle.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

Figure 1:
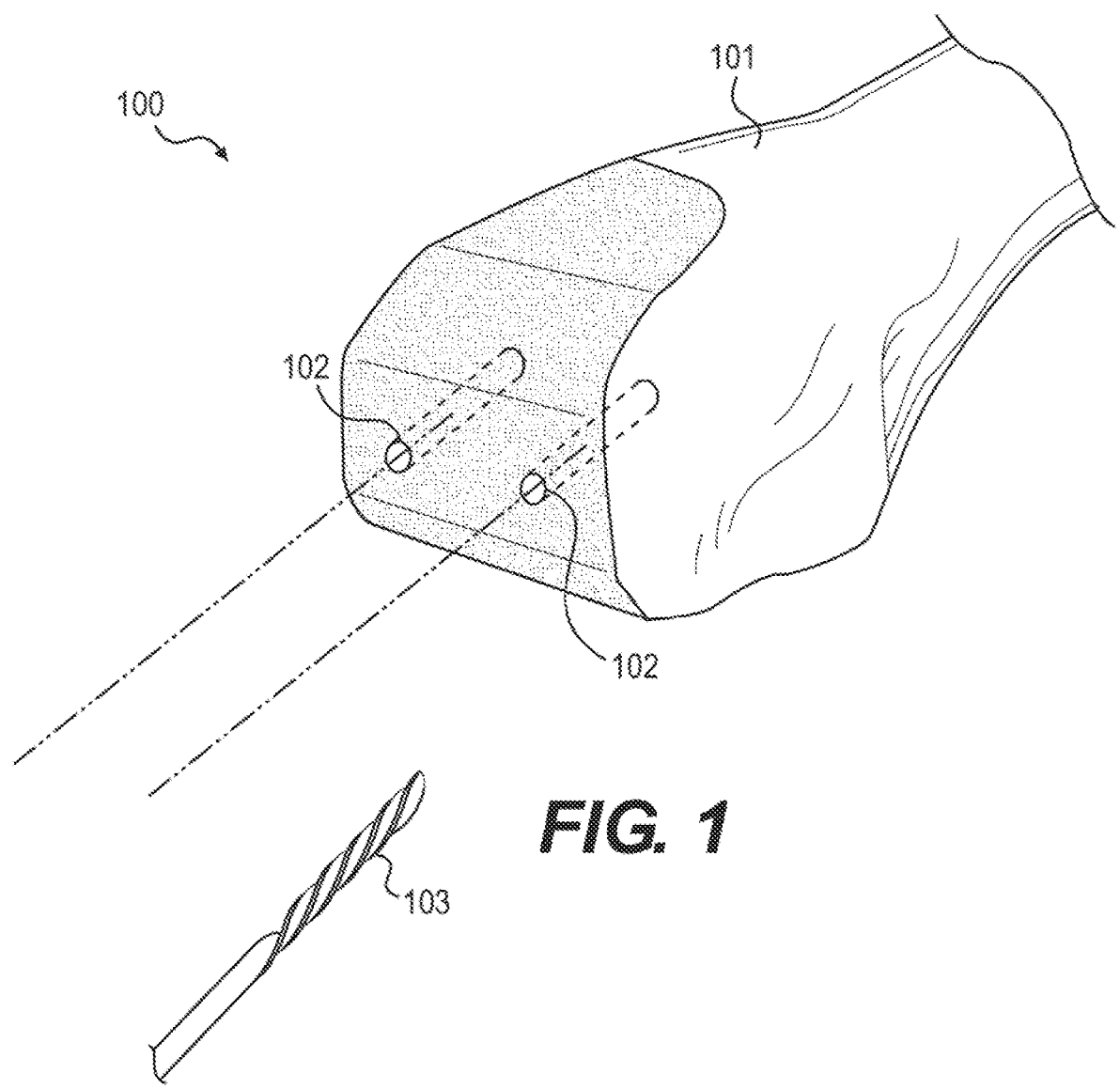
FIG. 1 provides a perspective view of an exemplary surgical procedure that may be performed consistent with the disclosed embodiments.

FIG. 1 illustrates an exemplary surgical environment 100 in which processes and methods consistent with the disclosed embodiments may be employed. As illustrated in FIG. 1, many surgical procedures, such as knee replacement procedures, require accurate and precise modification to the patient's anatomy. One such example is the placement of post or guide holes 102 within a patient's femur 101 using a surgical instrument, such as drill (not shown), having a rotary cutting tool 103. Because these post or guide holes 102 correspond to projections on a prefabricated prosthetic implant (not shown), each hole should generally be accurately and precisely placed at a specific location, depth, and orientation within the patient's bone.

In order to ensure efficient and proper alignment of the post holes within the patient's anatomy, a computer-aided surgery (CAS) system may be used to generate a graphical representation of the surgical site and a corresponding virtual guide that may aid the surgeon in properly aligning the tool prior to interaction with patient's anatomy. The CAS system consistent with the present disclosure may also provide a haptic feedback geometry that captures the surgical tool while the tool approaches the engagement site. Once captured, the boundaries of the virtual haptic geometry may limit or restrict the movement of the surgical instrument within the confines of a haptic volume defined by the virtual haptic geometry. Based on the surgeon's movements, the haptic volume may be gradually reduced, limiting the range of motion of the surgical instrument until the surgical tool is aligned with the target access associated with the post holes. Systems and methods for aligning the surgical instrument consistent with the disclosed embodiments are discussed in greater detail below and in the accompanying drawings.

As explained, many CAS systems include software that allows users to electronically register certain anatomic features (e.g., bones, soft tissues, etc.), surgical instruments, and other landmarks associated with the surgical site. CAS systems may generate a graphical representation of the surgical site based on the registration of the anatomic features. The CAS software also allows users to plan certain aspects of the surgical procedure, and register these aspects for display with the graphical representation of the surgical site. For example, in a knee joint replacement procedure, a surgeon may register target navigation points, the location and depth of bone and tissue cuts, virtual boundaries that may be associated with a corresponding reference for the application of haptic force, and other aspects of the surgery.

Figure 2:
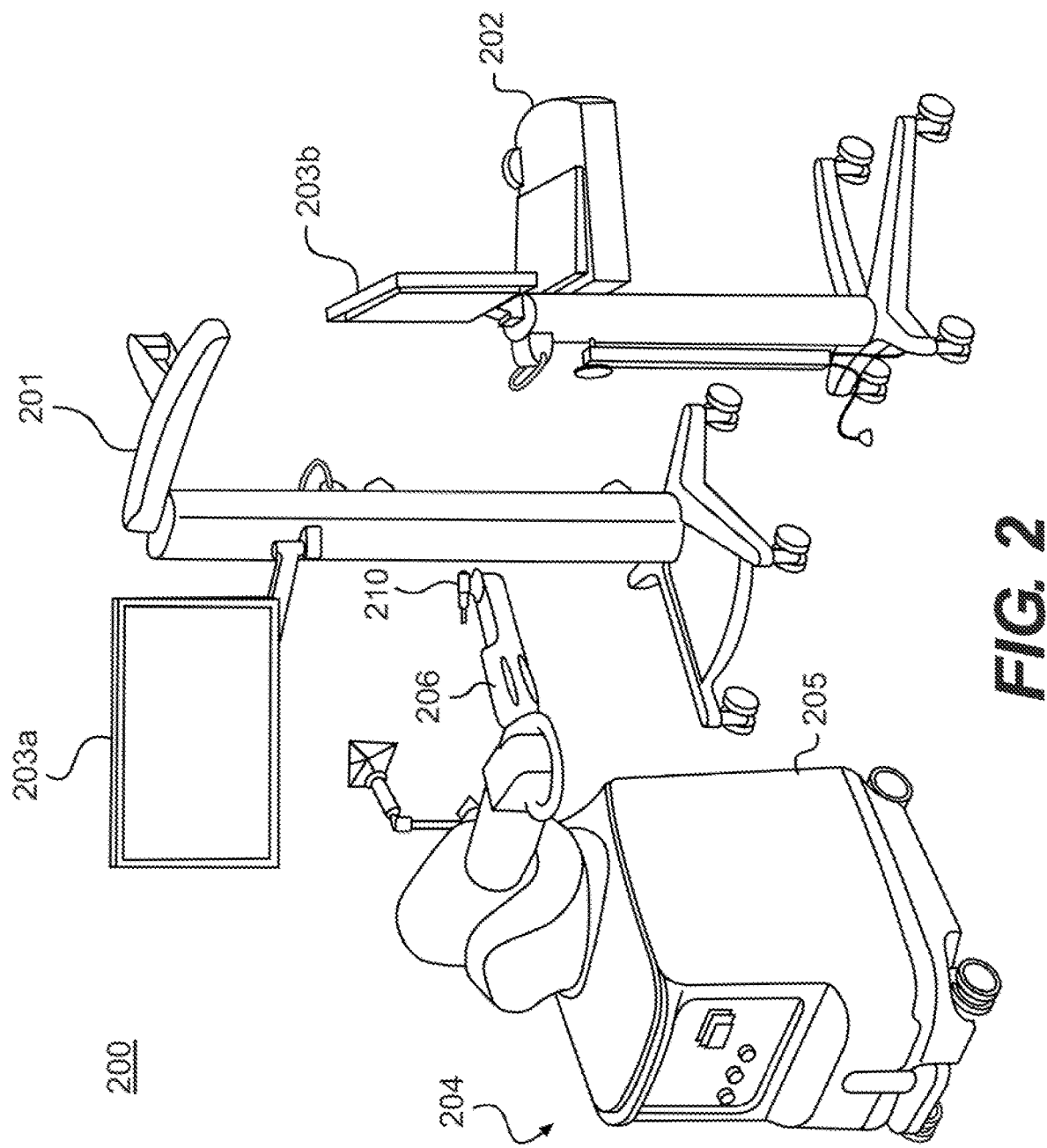
FIG. 2 provides a schematic illustration of an exemplary computer-assisted surgery (CAS) system, in which certain methods consistent with the disclosed embodiments may be implemented.

FIG. 2 provides a schematic diagram of an exemplary computer-assisted surgery (CAS) system 200, in which processes and features associated with certain disclosed embodiments may be implemented. CAS system 200 may be configured to perform a wide variety of orthopedic surgical procedures such as, for example, partial or total joint replacement surgeries. As illustrated in FIG. 2, CAS system 200 may comprise a tracking system 201, computer-assisted navigation system 202, one or more display devices 203a, 203b, and a robotic arm 204. It should be appreciated that CAS system 200, as well as the methods and processes described herein, may be applicable to many different types of joint replacement procedures. Although certain disclosed embodiments may be described with respect to knee replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic arm 204 can be used in an interactive manner by a surgeon to perform a surgical procedure, such as a knee replacement procedure, on a patient. As shown in FIG. 2, robotic arm 204 includes a base 205, an articulated arm 206, a force system (not shown), and a controller (not shown). A surgical tool 210 (e.g., an end effector having an operating member, such as a saw, reamer, or burr) may be coupled to the articulated arm 206. The surgeon can manipulate the surgical tool 210 by grasping and manually moving the articulated arm 206 and/or the surgical tool 210.

The force system and controller are configured to provide control or guidance to the surgeon during manipulation of the surgical tool. The force system is configured to provide at least some force to the surgical tool via the articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale, Fla. The force system and controller may be housed within the robotic arm 204.

Tracking system 201 may include any suitable device or system configured to track the relative locations, positions, orientations, and/or poses of the surgical tool 210 (coupled to robotic arm 204) and/or positions of registered portions of a patient's anatomy, such as bones. Such devices may employ optical, mechanical, or electromagnetic pose tracking technologies. According to one embodiment, tracking system 201 may comprise a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during a joint replacement procedure, navigation system 202 may display images related to the surgical procedure on one or both of the display devices 203a, 203b.

Figure 3:
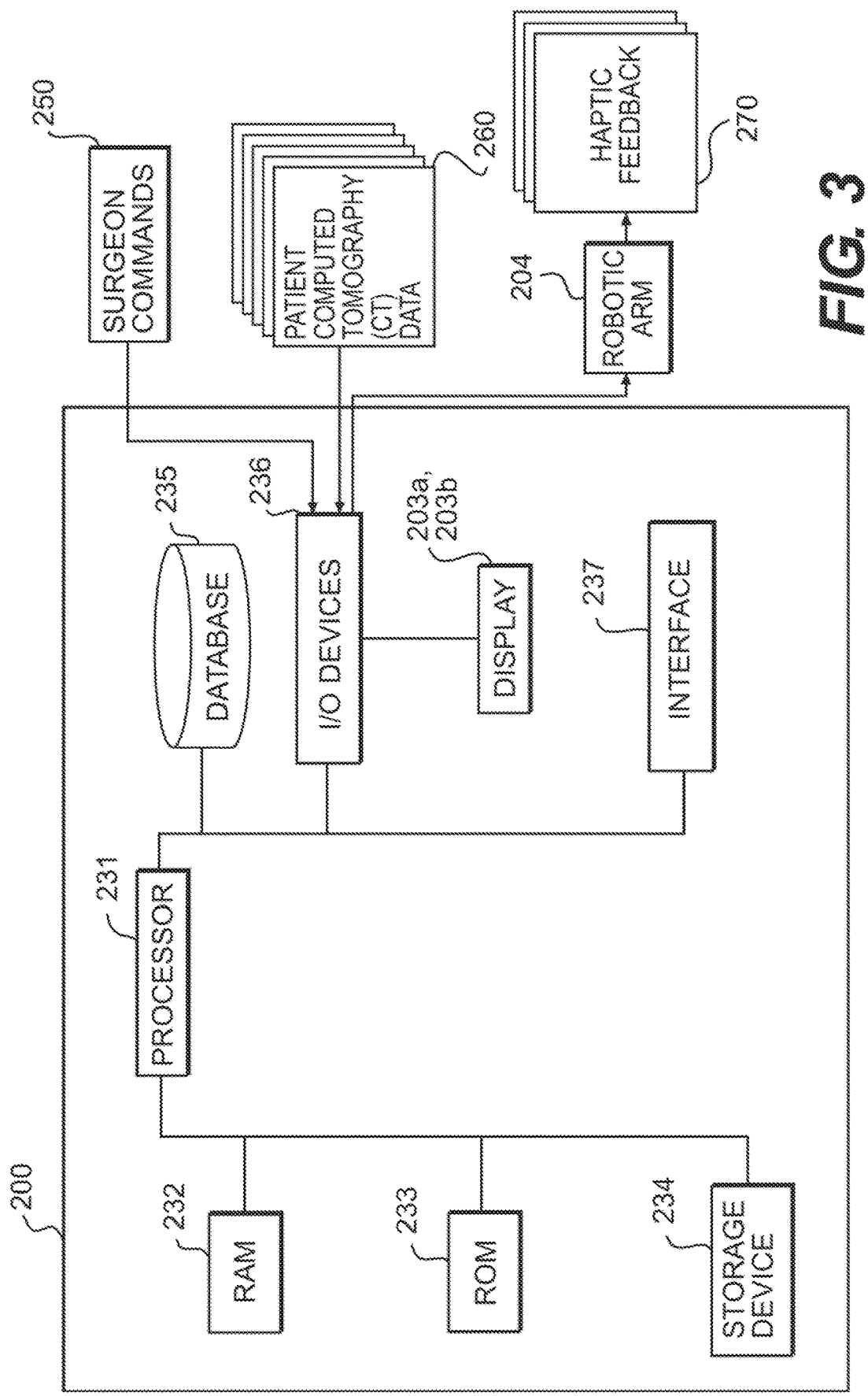
FIG. 3 provides a schematic diagram of an exemplary computer system, which may be used in one or more components associated with the CAS system illustrated in FIG. 2.

Navigation system 202 (and/or one or more constituent components of CAS system 200) may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as, tracking software, surgical navigation software, 3-D bone modeling or imaging software, and/or software for establishing and modifying virtual haptic boundaries for use with a force system to provide haptic feedback to surgical tool 210. For example, CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 2, processor 231 may be communicatively coupled to RAM 232, ROM 233, storage device 234, database 235, I/O devices 236, and network interface 237. Processor 231 may be configured to execute sequences of computer program instructions to perform various processes, which will be described in detail below. The computer program instructions may be loaded into RAM for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202, to perform functions or tasks associated with CAS system 200. For example, computer readable media may include instructions for causing the CAS system 200 to perform one or more methods for determining changes in parameters of a hip joint after a hip arthroplasty procedure. Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203a, 203b, including a graphical user interface (GUI) for outputting information on a monitor. I/O devices 236 may also include peripheral devices such as, for example, a printer for printing information associated with CAS system 236, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., bones) in software.

Processor 231 associated with CAS system 200 may be configured to establish a virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site.

In addition to physical objects, CAS system 200 may be configured to generate virtual objects—objects that exist in a software space and which may be useful during the performance of a surgical procedure. For example, CAS system 200 may be configured to generate virtual boundaries that correspond to a surgeon's plan for preparing a bone, such as boundaries defining areas of the bone that the surgeon plans to cut, remove, or otherwise alter. Alternatively or additionally, CAS system 200 may define virtual objects that correspond to a desired path or course over which a portion of surgical tool 210 should navigate to perform a particular task.

Figure 4:
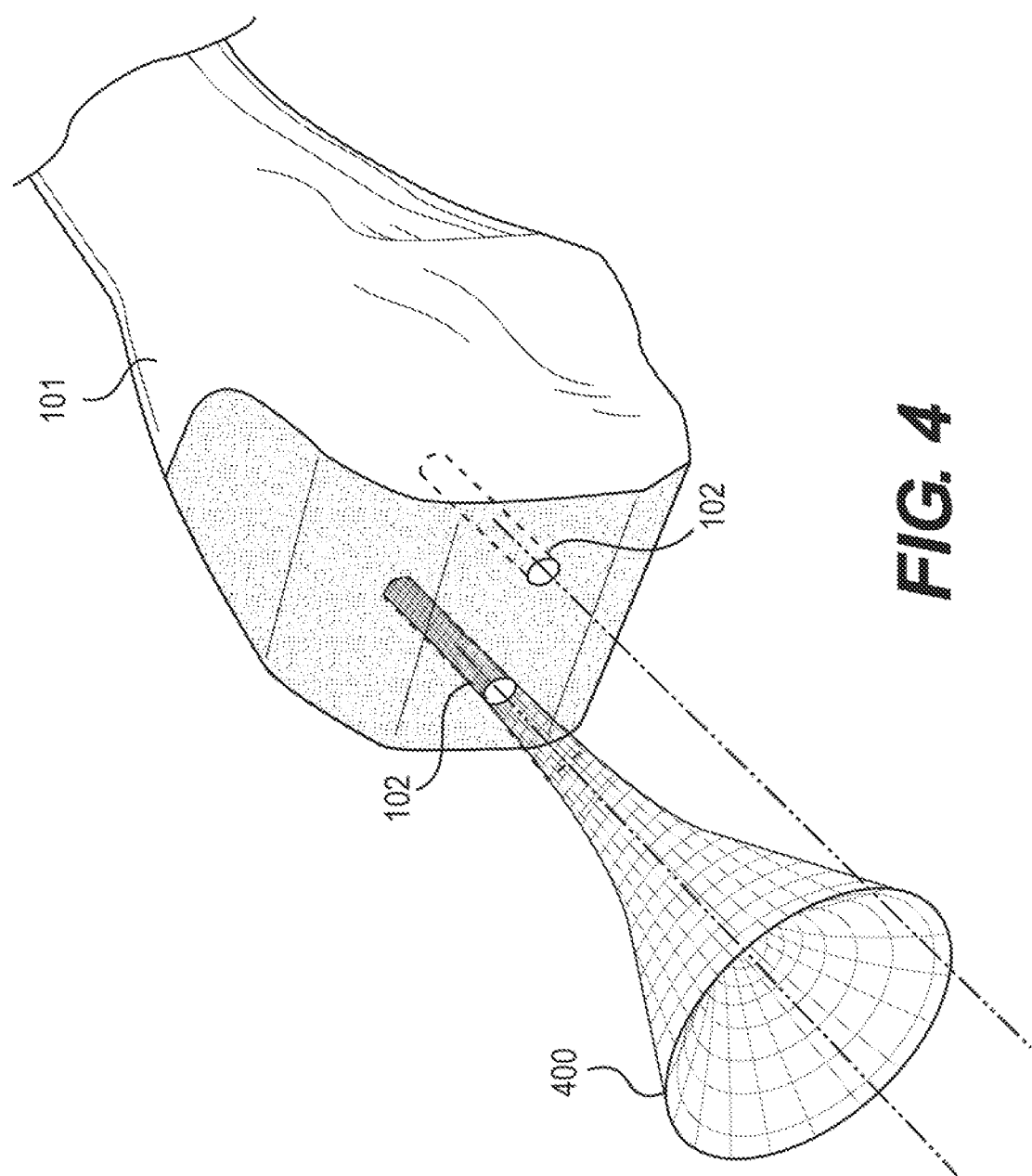
FIG. 4 provides an illustration of an exemplary virtual haptic volume, consistent with certain disclosed embodiments.
Figure 5:
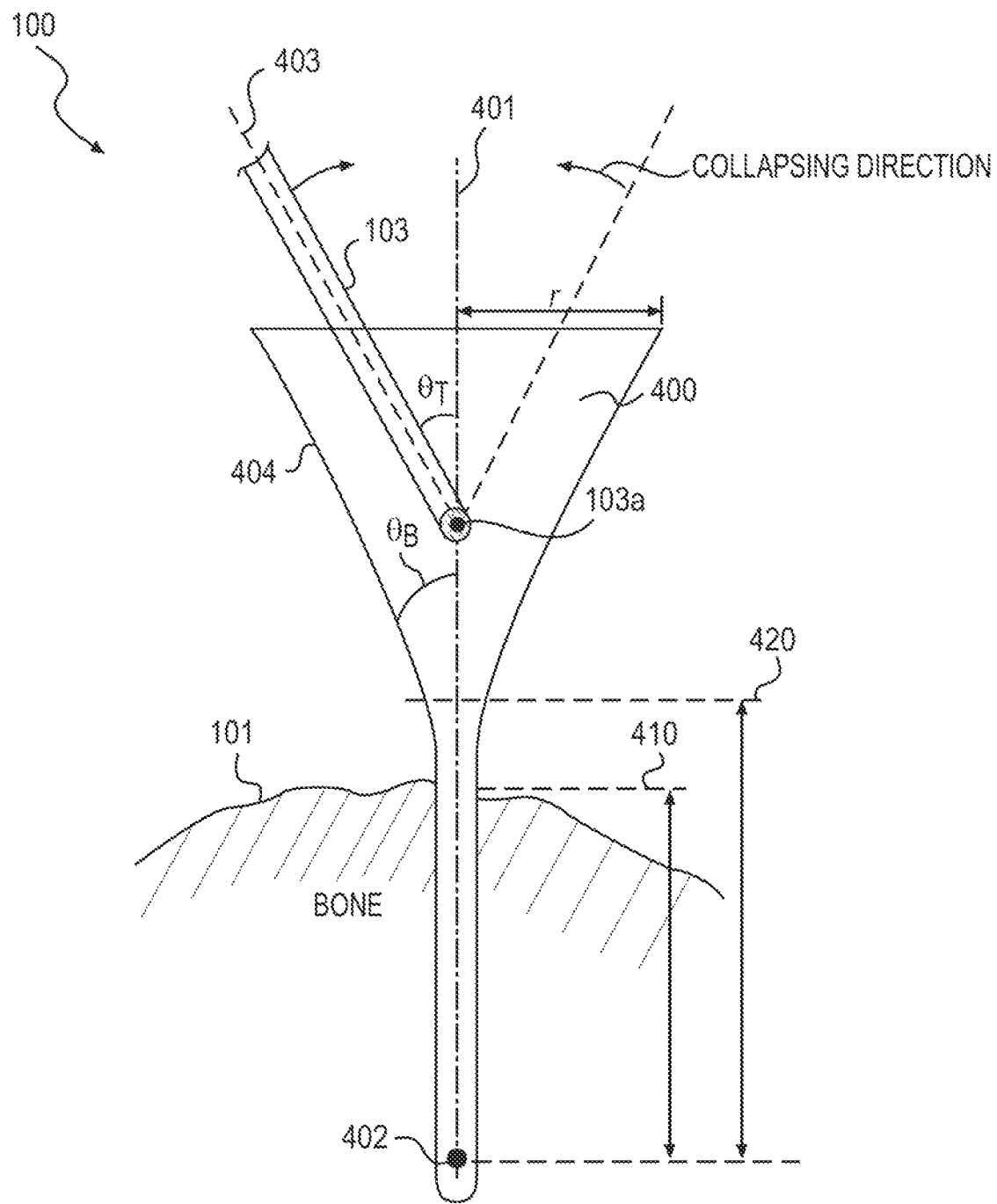
FIG. 5 provides a 2-dimensional side view of a virtual haptic volume, consistent with the disclosed embodiments.

According to one embodiment, CAS system 200 may be configured to generate a virtual haptic geometry that defines a point, line, surface, or volume in a virtual coordinate space. The virtual haptic geometry may be associated with a haptic feedback or force system of CAS system 200 such that, when a tracked position of a portion of the surgical tool (e.g., an established center point 103a or tool axis 403 of cutting tool 103) interacts with the virtual haptic geometry, a haptic force feedback is generated and applied to surgical tool 210. FIGS. 4 and 5 provide alternate views of an exemplary virtual haptic geometry 400 that may be generated consistent with the presently disclosed embodiments.

According to one exemplary embodiment, and as illustrated in FIG. 4, virtual haptic geometry 400 may be a substantially funnel-shaped volume that is positioned and oriented relative to a patient's anatomy, such as femur 101. As such, virtual haptic geometry 400 may define a virtual pathway to quickly and efficiently guide and position a surgical instrument, such as rotary drill or burr, into a proper alignment relative to femur 101 prior to engagement with femur 101. According to the embodiment illustrated in FIG. 4, virtual haptic geometry may comprise a substantially cone-shaped portion that converges toward a substantially cylindrically-shaped portion. The cylindrically-shaped portion may extend toward a target point (402 in FIG. 5), which, in the example illustrated in FIG. 4, corresponds to the depth of post holes 102.

Figure 8:
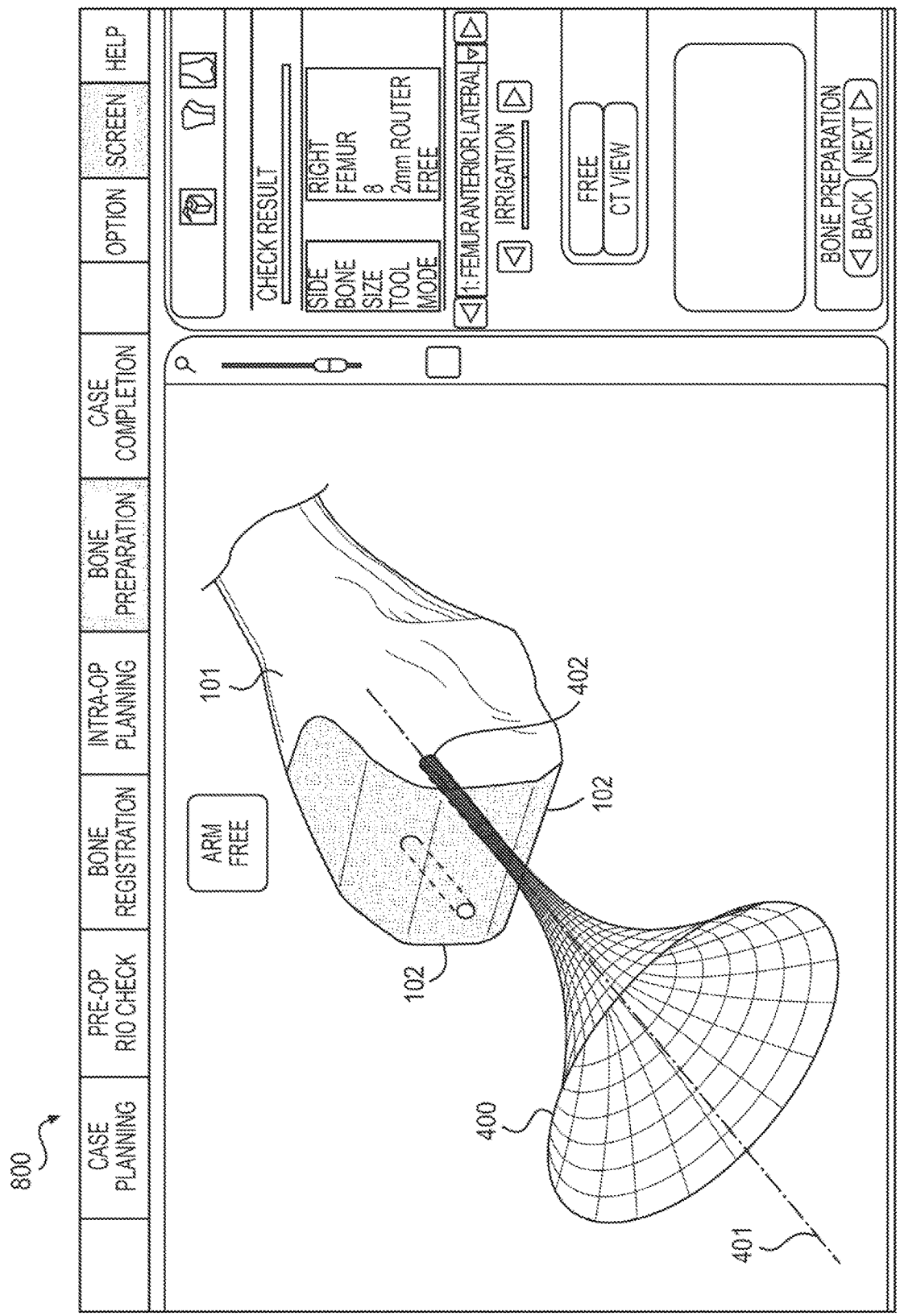
FIG. 8 illustrates an exemplary screen shot of a user interface that may be displayed during a surgical procedure, in accordance with certain exemplary disclosed embodiments.

FIG. 5 illustrates a side view of the exemplary virtual haptic geometry 400 shown in FIG. 4, being accessed by cutting tool 103. As illustrated in FIG. 5, virtual haptic geometry 400 may be defined about a target axis 401 that includes a target point 402. Virtual haptic geometry 400 may comprise a boundary surface 404, which may be positioned at an initial boundary angle, $\theta_B$, relative to the target axis 401. According to the embodiment shown in FIG. 5, boundary surface 404 may define a substantially cone-shaped volume having an initial base radius, r. It should be noted, however, that, although the upper portion of virtual haptic geometry 400 is illustrated in certain embodiments as having a substantially cone-shaped boundary surface, it is contemplated that virtual haptic geometry 400 may include or embody any shape suitable for guiding a cutting tool 103 toward a target point 402. For example, as shown in FIG. 8, boundary surface 404 may define a substantially curved blending section, which is designed to converge toward the target axis more aggressively than the substantially linear boundary surface shown in FIG. 5.

Target point 402 may be a user-defined point that corresponds to the target destination of at least a portion of cutting tool 103. According to one embodiment, target point 402 may define a target depth 410 of post or guide hole 102 of femur 101. As such, target point 402 corresponds to a desired depth 410 that a reference point 103a of tool 103 (also referred to herein as a tool center point (TCP)) can reach before a haptic feedback force is applied to surgical tool 210.

Target axis 401 may include target point 402 and may serve as a central axis about which virtual haptic geometry 400 may be defined. Target axis 401 may also define a desired axis for approaching target point 402 with cutting tool 103. As such, target axis 401 may define the axis to which virtual haptic geometry 400 converges, and may correspond to the desired or ideal orientation of approach of surgical tool 403 toward target point 402.

Figure 5A:
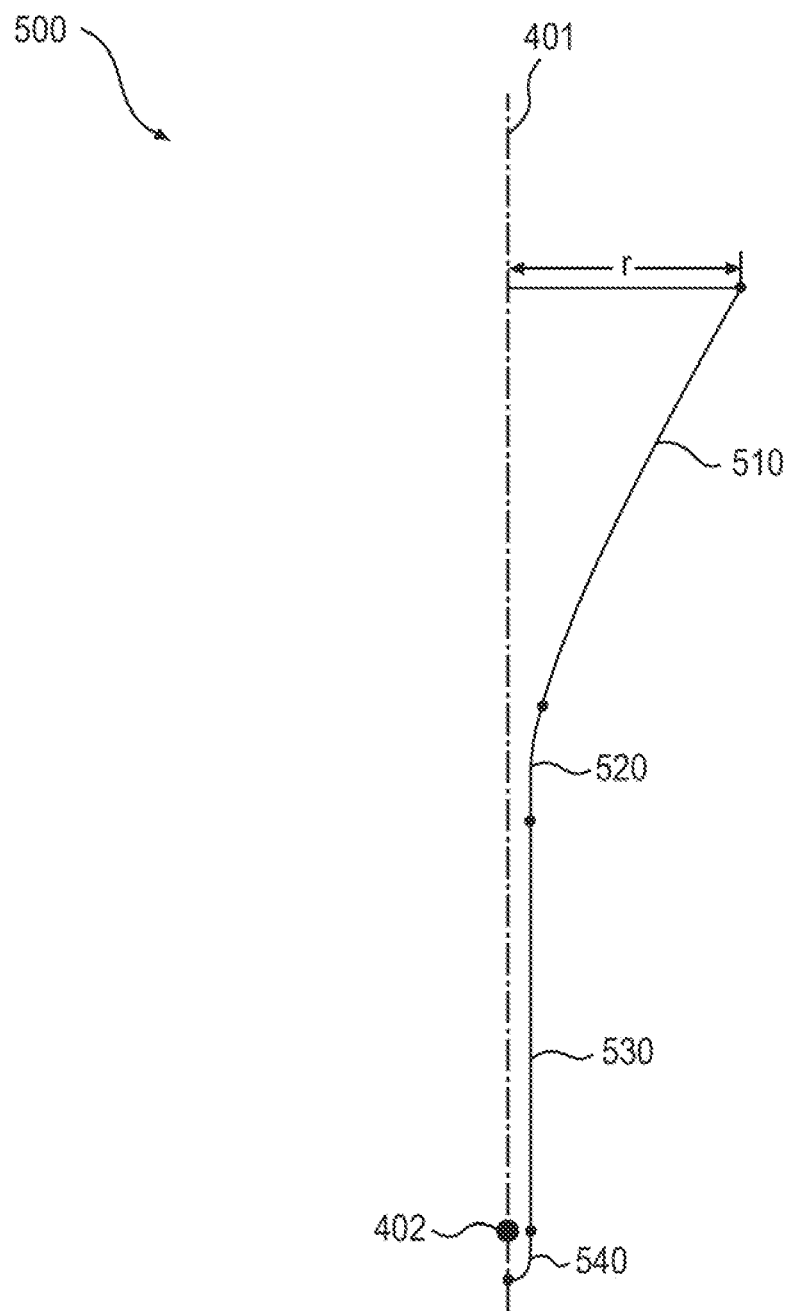
FIG. 5A provides a side view of an exemplary revolute shape that, when rotated about a target axis, defines the virtual haptic volume illustrated in FIG. 5.

FIG. 5A illustrates an side view of an exemplary revolute shape that is used to create the funnel-shaped virtual haptic geometry 400 illustrated in FIG. 5. As illustrated in FIG. 5, virtual haptic geometry 400 may be rotationally symmetric about target axis 401. As such, CAS system 200 may be configured to generate virtual haptic geometry 400 by creating a revolute shape that defines the profile of the desired boundary surface 404 of virtual haptic geometry 400. Once the shape of the revolute is defined, CAS system 200 may be configured to virtually rotate the revolute shape about target axis 401, defining boundary surface 404 of virtual haptic geometry 400.

As illustrated in FIG. 5A, the funnel-shaped haptic volume shown in FIG. 5 may be created by first defining the revolute shape that will be rotated about a target axis 401. The shape may comprise a first substantially linear segment 510 that is oriented at an angle that defines the desired base radius, r, of the funnel portion. Linear segment 510 may converge toward target axis 401 as it approaches a second linear segment 530.

Second linear segment 530 may be parallel with target axis 401 and may be configured to define the desired radius of the cylindrical portion of virtual haptic geometry 400. According to one embodiment, the distance between target axis 401 and second linear segment 530 may correspond to the desired radius of post hole 102 (which corresponds to the radius of a stabilizing element of a prosthetic implant that is to fit within post hole 103). A substantially curved (or circularly blended) segment 520 may be included for providing a gradual transition between first and second linear segments 510, 530. This gradual transition limits the perception of an abrupt "edge" that would otherwise be associated with a haptic surface defined by the intersection of two linear segments.

The revolute shape 500 consistent with the disclosed embodiments may also comprise a bottom segment 540 that defines the bottom of target post hole. In the embodiment illustrated in FIG. 5A, the bottom segment is substantially curved about target point 402, corresponding to radius of the burr associated with cutting tool 103. Once the revolute is complete, software associated with CAS system 200 may generate the funnel-shaped virtual haptic boundary 400 by rotating revolute shape 500 about target axis 401.

It is contemplated, however, that, as an alternative or in addition to the funnel-shaped haptic volume shown in FIG. 5 (and the corresponding revolute shown in FIG. 5A for generating the same) are exemplary only and not intended to be limiting. Indeed, CAS system 200 may provide additional and/or different revolute shapes and processes for creating collapsing virtual haptic geometries for guiding surgical instruments toward a planned target orientation and target point.

During operation of CAS system 200 and in accordance with an exemplary embodiment, virtual haptic geometry 400 becomes associated with cutting tool 103 when reference point 103a of cutting tool 103 enters the volume defined by virtual haptic geometry. Once active, virtual haptic geometry 400 may be configured to provide a haptic feedback when cutting tool 103 interacts with one or more virtual boundaries 404. For example, virtual haptic geometry 400 may define a haptic "wall" that constrains, inhibits, or prevents cutting tool 103 and/or reference point 103a from moving beyond the boundary surface 404 of virtual haptic surface 400. In an exemplary embodiment, virtual haptic geometry 400 may be configured with an "opening" for allowing cutting tool 103 to disengage from virtual haptic geometry 400. While this disengagement opening may be located anywhere along virtual haptic geometry 400, an exemplary embodiment includes the opening along the surface of virtual haptic geometry 404 that is located farthest from bone or tissue surfaces of the patient. In the embodiment illustrated in FIG. 5, the top surface of boundary surface 404 may be configured as the disengagement opening.

As an alternative or in addition to constraining the movement of cutting tool 103 (and/or tool reference point 103a) from the volume defined by virtual haptic geometry 400, CAS system 200 may be configured to guide cutting tool 103 toward a desired orientation prior to engagement with femur 101. Specifically, CAS system 200 may be configured to monitor a tool orientation angle, $\theta_T$, which comprises an orientation angle of the tool axis 403 that is determined based on an orientation of a target axis 401. According to one embodiment, such as that illustrated in FIG. 5 in which the tool axis 403 is located within the same plane as the target axis 401, the orientation angle, $\theta_T$, which comprises the angle between tool axis 403 and target axis 401.

However, when tool axis is not located in the same plane as target axis 401 (as it is in FIG. 5), the tool orientation angle, $\theta_T$, comprises the angle formed by the tool axis and a line parallel to target axis 401 that is co-planar with tool axis. According to the exemplary embodiment, the line parallel to target axis may be normal to a plane that is normal to target axis 401. In this embodiment, although the tool orientation angle, $\theta_T$, is not directly determined with respect to the target axis, it is based on the relative orientation of target axis within virtual software space. As will be explained in further detail below, CAS system 200 may be configured to facilitate alignment of the tool axis 403 with target axis 401 by modifying the location of boundary surface 404 of virtual haptic geometry 400 based on the location of tool axis 403.

To ensure that cutting tool is positioned in the proper orientation prior to engagement with a surface of the patient's anatomy, an intermediate haptic threshold may be established and associated with virtual haptic boundary 400. Specifically, the virtual haptic boundary 400 may include an intermediate tool stop haptic plane 420 that provides haptic feedback if reference point 103a attempts to advance without being in the proper orientation. The haptic feedback may include a haptic wall that constrains advancement of cutting tool 103 past intermediate tool stop haptic plane 420 if one or more of tool axis 403 and/or tool reference point 103a is not aligned with target axis 401.

As explained, software associated with CAS system 200 may be configured to register and track certain aspects of surgical environment 100. For example, cutting tool 103, along with other features of surgical environment 100, may be registered and associated with a virtual coordinate space for tracking and display by CAS system 200. As such, tracking system 201 of CAS system 200 can determine the relative position and orientation of cutting tool 103 in the virtual coordinate space.

In order to properly monitor the orientation of tool axis 403 of cutting tool 103, the tool axis 403 of cutting tool 103 may first be registered for tracking in virtual coordinate space of CAS system 200. According to one embodiment (such as that illustrated in FIG. 5), tool axis 403 may correspond to the central axis of a rotary burr, which passes through reference point 103a associated with the center of the tip of the rotary burr. Tool axis 403, along with reference point 103a, may be determined during a calibration process of CAS system 200, prior to the surgical procedure. Alternatively or additionally, CAS system 200 may be registered as part of the registration process during the surgical procedure by using a pre-calibrated registration probe to capture and record the locations of a plurality of points along tool axis 403. Because the position of the axis at the surface of the cylindrically-shaped rotary burr is slightly different than the position of the axis at the true center of tool axis 403, CAS system 200 may be provided with an offset to project the tool axis 403 to the center of cutting tool 103.

According to yet another embodiment, the pre-calibrated registration probe may be used to capture a large number of points along the surface of cutting tool 103. Based on the relative locations of these points, software associated with CAS system 200 may be configured to derive tool axis 403. It is contemplated that additional and/or different methods may be used for registering various aspects of cutting tool 103 than those that are listed above. For example, a virtual software model representing cutting tool 103 may be generated using computed tomography (CT) scan information. The model may be registered in the virtual coordinate space using the calibrated registration probe. Once registered, tracking system 201 associated with CAS system 200 can monitor the real-time location, position, and orientation of registered components of surgical environment 100 relative to the established virtual coordinate space in order to guide cutting tool 103 to target depth points 402a-402c by sequentially activating each of target depth points 402a-402c in accordance with the processes and methods consistent with the disclosed embodiments.

Processes and methods consistent with the disclosed embodiments provide a solution for quickly and efficiently guiding cutting tool 103 to a proper orientation for engagement with a patient's anatomy. Features consistent with the disclosed embodiments track the position and orientation of a tool axis based on the relative orientation of target axis 401. As explained, CAS system 200 may be configured to monitor a tool orientation angle, $\theta_T$, which comprises an orientation angle of the tool axis 403 that is determined based on an orientation of a target axis 401. According to one embodiment, such as that illustrated in FIG. 5 in which the tool axis 403 is located within the same plane as the target axis 401, the orientation angle, $\theta_T$, which comprises the angle between tool axis 403 and target axis 401.

However, when tool axis is not located in the same plane as target axis 401 (as it is in FIG. 5), the tool orientation angle, $\theta_T$, comprises the angle formed by the tool axis and a line parallel to target axis 401 that is co-planar with tool axis. According to the exemplary embodiment, the line parallel to target axis may be normal to a plane that is normal to target axis 401. In this embodiment, although the tool orientation angle, $\theta_T$, is not directly determined with respect to the target axis, it is based on the relative orientation of target axis within virtual software space. As will be explained in further detail below, CAS system 200 may be configured to facilitate alignment of the tool axis 403 with target axis 401 by modifying the location of boundary surface 404 of virtual haptic geometry 400 based on the location of tool axis 403.

Figure 6:
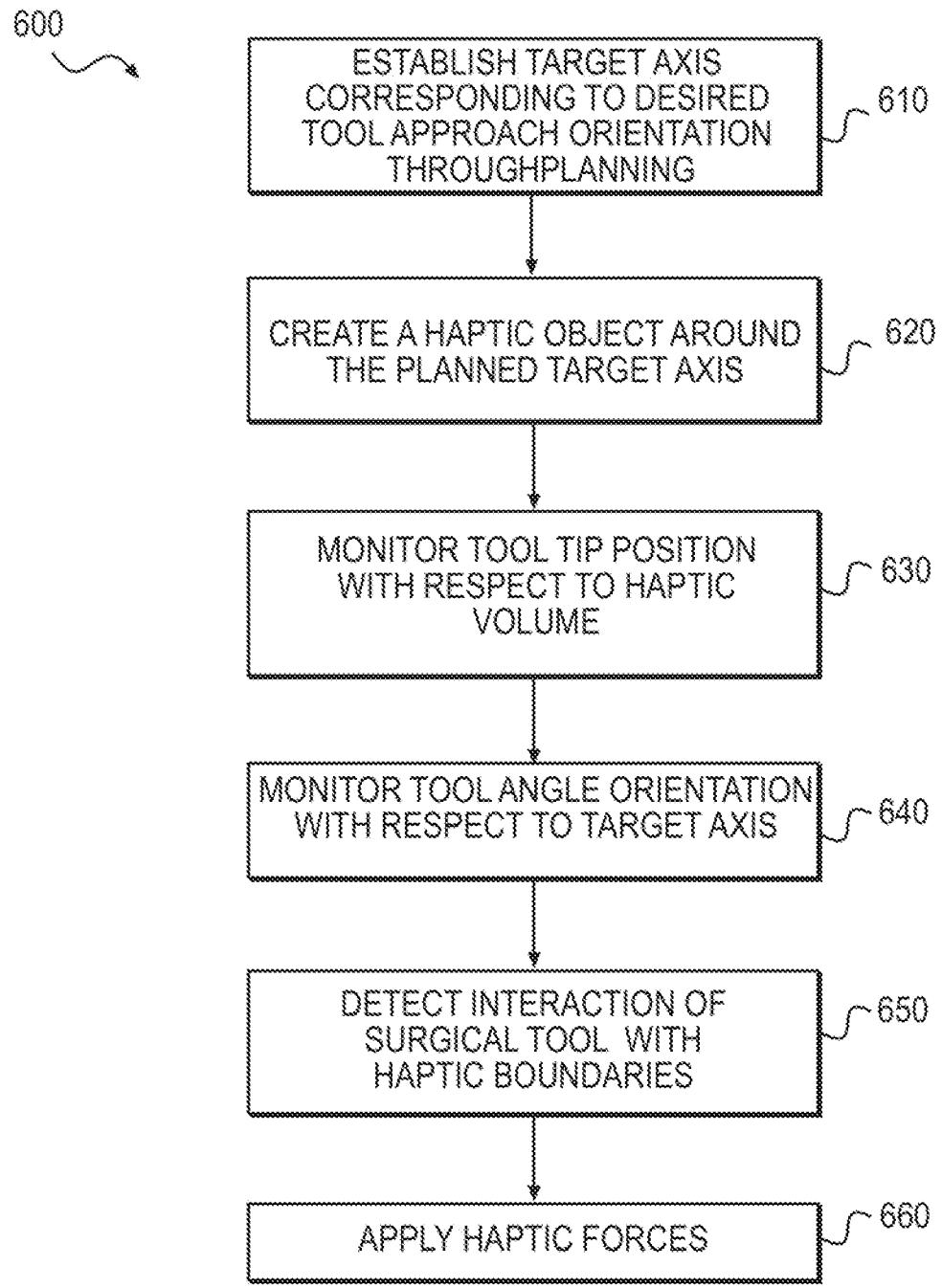
FIG. 6 provides a flowchart showing an exemplary method for establishing a virtual haptic surface, in accordance with certain disclosed embodiments.
Figure 7:
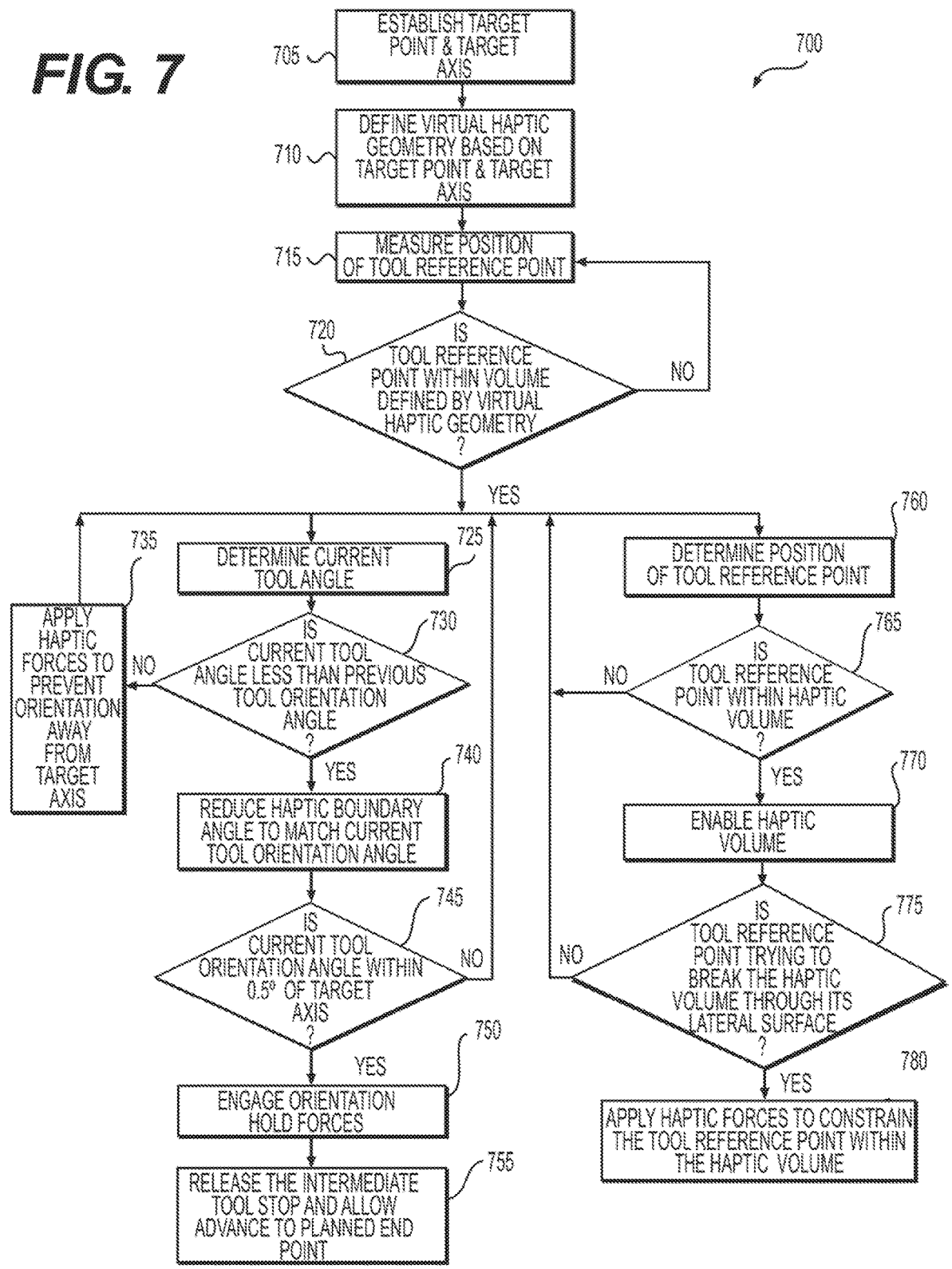
FIG. 7 provides a flowchart depicting an exemplary method for guiding an instrument using a virtual haptic geometry, consistent with certain disclosed embodiments.

Exemplary methods consistent with the disclosed embodiments track the position and orientation of tool axis 403 based on an orientation of target axis 401. As the orientation angle, $\theta_T$, becomes smaller, virtual haptic geometry 400 associated with surgical tool 210 is repositioned behind the virtual representation of cutting tool 103, creating a boundary surface that "collapses" as cutting tool 103 is brought into alignment with target axis 401. As a result, cutting tool 103 is discouraged, constrained, or prohibited from being rotated to an angle that is substantially greater than the smallest registered orientation angle. This "collapsing" virtual haptic geometry allows the surgeon the freedom to move or rotate cutting tool 103 only to those positions that bring cutting tool 103 in closer alignment with target axis 401. Eventually, as the surgeon rotates cutting tool 103 within the area defined by virtual haptic geometry 400, the boundary decreases in size until tool axis 403 is sufficiently aligned with target axis 401. FIGS. 6 and 7 provide flowcharts that illustrate exemplary methods for guiding a surgical instrument using haptic feedback consistent with the presently disclosed embodiments.

It is contemplated that, in accordance with certain embodiments, the collapsing cone virtual haptic boundary is configured to constrain cutting tool 103 from being moved to an angle that is substantially greater than the smallest registered orientation angle. Specifically, force feedback system may include or embody an impedance-type force feedback system that includes haptic boundaries having variable levels of perceived "stiffness." In one embodiment, the stiffness of virtual haptic boundary may be high, resulting in a haptic boundary that strictly constrains cutting tools from being moved to any angle this is greater than the smallest registered orientation angle.

In certain other embodiments, however, the stiffness of the virtual haptic boundary may be lowered to provide a "softer" haptic boundary. The resulting haptic boundary may constrain cutting tool from being moved to angles that are substantially greater than the smallest registered orientation. In this embodiment, virtual haptic boundary may allow some flexibility for cutting tool to exceed the virtual haptic boundary, while substantially constraining cutting tool in accordance with the virtual haptic boundary.

FIG. 6 provides a flowchart 600 illustrating an exemplary method for guiding a surgical instrument, in accordance with certain disclosed embodiments. As illustrated in FIG. 6, the process comprises establishing a target axis corresponding to a desired approach orientation for the tool (Step 610). According to one embodiment, target axis 401 may be established during the process of planning the placement of post holes 102 for receiving corresponding stabilizing projections (not shown) associated with a prosthetic implant. During the planning phase, a number of parameters associated with each of post holes 102 may be established such as, for example, the depth and diameter of the hole, the position of opening of the holes relative to the surface of the bone, and the orientation of hole within the bone.

Upon establishing the parameters for creating each of post holes 102, CAS system 200 may establish target point 402 and target axis 401 associated with each of post holes 102. Target point 402 may be configured to correspond to the depth that reference point 103a of cutting tool 103 should reach in order to complete a respective post hole. Similarly, target axis 401 may be generated as the desired or "ideal" approach orientation in which tool axis 403 of cutting tool should be maintained in order to create each of post holes 102 according to the planned parameters associated therewith.

Once target (i.e., planned) axis 401 has been established, a haptic object (e.g. virtual haptic boundary 400) may be created around target axis 401 (Step 620). According to one embodiment, virtual haptic boundary may be generated by rotating a linear shape corresponding to the desired profile of virtual haptic boundary 400 (such as the revolute shape shown in FIG. 5A) about target axis 401. In this way, virtual haptic boundary 400 is rotationally asymmetric about target axis 401.

Upon establishing and activating the haptic object associated with virtual haptic boundary 400, reference point 103a may be monitored with respect to the haptic volume defined by virtual haptic boundary 400 (Step 630). As explained, in order to properly monitor the orientation of tool axis 403 of cutting tool 103, reference point 103a and tool axis 403 of cutting tool 103 may first be registered for tracking in virtual coordinate space of CAS system 200. Reference point 103a may be established as the center of the tip of cutting tool 103 and may be tracked by tracking system 201 of CAS system 200 to estimate, among other things, the interaction between tip of cutting tool 103 with the patient's anatomy.

According to one exemplary embodiment, the position of reference point 103a may be used to activate haptic forces associated with virtual haptic boundary 400. For example, software associated with CAS system 200 may activate haptic forces associated with the boundary surface 404 of virtual haptic boundary 400 once reference point 103a is within the volume defined by virtual haptic boundary 400. Once the haptic forces have been activated, CAS system 200 may be configured to apply haptic forces to robotic arm 204 to constrain the movement of cutting tool 103 in certain situations.

In addition to monitoring the position of reference point 103a (e.g., the tip of cutting tool 103) the process comprises monitoring an orientation of a tool axis 403 of cutting tool 103. As explained, cutting tool 103, along with other features of surgical environment 100, may be registered and associated with a virtual coordinate space for tracking and display by CAS system 200. As such, tracking system 201 of CAS system 200 can determine the relative position and orientation of cutting tool 103 in the virtual coordinate space.

Upon determining the relative orientation of cutting tool 103, CAS system 200 may determine an orientation angle of cutting tool 103 relative to target axis 401 (Step 640). According to one embodiment, processor 231 associated with CAS system 200 may calculate the orientation angle ($\theta_T$ of FIG. 5) by determining the angular offset between the tracked position of tool axis 403 and target axis 401 in the virtual coordinate space.

Once the orientation angle of tool axis 403 has been determined, the established haptic boundary (e.g., virtual haptic geometry 400) may be modified and/or re-generated based on the orientation angle of tool axis 403. As explained, the haptic boundary may embody a virtual surface at which a haptic force may be applied to cutting tool 103 in response to an interaction of the virtual representation of cutting tool 103 with virtual surface 404. The haptic boundary may be positioned in virtual (software) space relative to the virtual representation of cutting tool 103 so as to constrain cutting tool 103 from being rotated to an angle greater than the orientation angle of tool axis 403.

As the orientation angle, $\theta_T$, decreases, the virtual haptic geometry 400 associated with cutting tool 103 collapses behind tool axis 403, thereby causing the virtual haptic geometry 400 to converge on target axis 401. As such, when the tool orientation angle, $\theta_T$, is 0 (tool axis 403 parallel (or co-linear) to target axis 401, virtual haptic geometry 400 completely surrounds surgical instrument 403, thereby locking surgical instrument 403 into place. According to one exemplary embodiment, CAS system 200 may apply, if the tool orientation angle, $\theta_T$, is less than a threshold angle, a haptic force that constrains cutting tool 103 to a position that brings tool axis 403 in parallel with target axis 401. According to an exemplary embodiment, threshold angle may be established as an angle between 0.3 and 3 degrees.

Upon establishing the haptic boundary relative to the tool axis of cutting tool 103, CAS system 200 may be configured to detect an interaction of cutting tool 103 with the haptic boundary (Step 650). More specifically, CAS system 200 may be configured to detect an interaction between reference point 103a associated with the tip of cutting tool 103 with a boundary surface 404 of the virtual haptic geometry. Alternatively or additionally, CAS system 200 may be configured to detect an interaction between a portion of tool axis 403 with the surface of virtual haptic geometry 400.

After detecting interaction of cutting tool 103 with virtual haptic geometry 400, a haptic force may be applied to the cutting tool 103 (Step 650). For example, should a surgeon try to rotate cutting tool 103 to an angle greater than the surface angle of virtual haptic geometry 400 (which has been repositioned to correspond to the minimum registered orientation angle of cutting tool 103), force system of CAS system 200 may apply a haptic force to discourage, constrain, or prevent the surgeon from rotating beyond the surface angle of virtual haptic geometry 400.

The embodiment illustrated and described with respect to FIG. 6 provides an exemplary embodiment for guiding cutting tool 103 into a proper orientation (e.g., parallel with target axis 401) for approaching target point 402. FIG. 7 provides a flowchart 700 illustrating another exemplary method for guiding a cutting tool 103 to a target orientation and, ultimately, a target point 402.

As illustrated in FIG. 7, the method may commence upon establishing a target point 402 and target axis 401 in the virtual coordinate system associated with surgical environment 100 (Step 705). For example, a user (e.g., a surgeon, surgical technician, etc.) of CAS system 200 may define a target point 402 using a graphical user interface associated with CAS system 200. Target point 402 may correspond to a location at which at least a portion of cutting tool 103 should reach during a surgical procedure. According to the embodiment illustrated in FIG. 5, target point 402 may be defined within a patient's femur 101 as the desired depth 410 of a post hole 102 that will receive a stabilizing post of a prosthetic femoral component.

Once target point 402 has been established, target axis 401 may be defined. As with target point 402, the user of CAS system 200 may define the target axis 401 using the graphical interface of CAS system 200. Target axis 401 may be selected as the line that corresponds with a desired approach orientation of cutting tool 103 to target point 402. In the case of a post hole, this desired approach orientation corresponds with the desired orientation of the hole within the patient's anatomy, which, in turn, may correspond to the orientation of the stabilizing projections of a prosthetic implant.

Upon establishing the target point 402 and target axis 401, CAS system 200 may define a virtual haptic geometry (Step 710). According to one embodiment, CAS system 200 may generate a funnel-shaped virtual haptic geometry that is centered around target axis 401 and converges toward target point 402. The virtual haptic geometry may comprise a substantially cone-shaped upper portion that tapers toward a substantially cylindrically-shaped lower portion, such as illustrated in FIG. 4. Alternatively or additionally, the virtual haptic geometry may comprise a substantially curved blending section similar to that illustrated in FIG. 8.

Regardless of its specific shape, virtual haptic geometry 400 comprises a haptic boundary surface 404 that defines a boundary at which a virtual haptic force is applied. That is, when cutting tool 103 is located or "captured" within the volume defined by the virtual haptic geometry 400, attempts to move cutting tool 103 outside of the volume will be met by an opposing force applied at the haptic surface by force system of CAS system 200. Cutting tool 103 may be able to exit the haptic volume at a predetermined exit point that, according to one embodiment, is typically the base of the inverted cone shape, directly opposite the direction of convergence of virtual haptic geometry 400.

After virtual haptic geometry 400 has been defined, the position of a reference point 103a associated with cutting tool 103 may be determined (Step 715). Specifically, as explained above, tool axis 403 and reference point 103a may be registered in a virtual coordinate space relative to other landmarks associated with surgical environment 100. As such, tracking system 201 of CAS system 200 may be configured to monitor the position of reference point 103a. This position may be displayed on one or more displays 203a, 203b of CAS system 200 for viewing by the surgeon. Regardless of whether reference point 103a is viewed or tracked via display(s) 203a, 203b, CAS system 200 may electronically monitor the position of reference point 103a in the virtual coordinate space.

CAS system 200 may compare the position of the tool reference point 103a with a location of a boundary surface 404 of virtual haptic geometry to determine whether tool reference point 103a is located within the volume defined by the virtual haptic geometry (Step 720). Specifically, CAS system 200 may compare the relative position of tool reference point 103a within the virtual coordinate system with the relative position of boundary surface 404. If the tool reference point 103a is not within the volume defined by the virtual haptic geometry (Step 720: No), CAS system 200 may revert back to step 715 and continue monitoring the position of tool reference point 103a.

If, on the other hand, tool reference point 103a is within the volume defined by virtual haptic geometry 400 (Step 720: Yes), CAS system 200 may determine a current orientation angle ($\theta_T$) of cutting tool 103 (Step 725). As explained above, tool axis 403 of cutting tool 103 may be registered in a virtual coordinate space relative to other landmarks associated with surgical environment 100. As such, tracking system 201 of CAS system 200 may be configured to monitor the orientation of tool axis 403 within the virtual coordinate space. Based on the orientations of tool axis 403 and orientation of target axis 401 in virtual coordinate space, CAS system 200 may be configured to determine an orientation angle, $\theta_T$, of tool axis 403 relative to target axis 401.

CAS system 200 may then be configured to compare the current orientation angle, $\theta_T$, associated with cutting tool 103 with a previous tool orientation angle (Step 730). According to one embodiment, tracking system 201 of CAS system 200 may be configured to monitor and record the current position and orientation of cutting tool 103, while storing previously-monitored position and orientation information in memory. Accordingly, CAS system 200 can compare the current position and orientation of cutting tool 103 with a previous position and orientation of cutting tool 103.

If the current tool orientation angle, $\theta_T$, is not less than the previous tool orientation (Step 730: No), CAS system 200 may apply haptic forces to robotic arm 204 to prevent or constrain the movement of cutting tool 103 from being positioned in an orientation that is further away from the target axis. If, on the other hand, the tool orientation angle, $\theta_T$, is less than a previous orientation angle (Step 730: Yes), CAS system 200 may modify the haptic geometry to reduce the haptic boundary angle to match the current tool orientation angle, $\theta_T$ (Step 740). More specifically, CAS system 200 may modify the orientation and/or position of boundary surface 404 to correspond with the orientation and/or position of tool axis 403. For example, using the embodiment illustrated in FIG. 5 as an example, CAS system 200 may modify the position and angle of boundary surface 404 so that boundary surface 404 collapses behind tool axis 403. In other words, boundary surface 404 may be repositioned to include tool axis 403. By modifying the position of boundary surface 404 relative to a corresponding decrease in orientation angle of tool axis 403 relative to target axis 401, CAS system 200 constrains cutting tool 103 from being rotated at an angle greater than the smallest registered orientation angle of surgical axis 403.

CAS system 200 may then determine whether the current tool orientation angle is within a predetermined threshold angle of target axis 401 (Step 745). This predetermined threshold may be a user-defined threshold that represents an acceptable amount of deviation between a current tool axis 403 and target axis 401. According to one embodiment, the predetermined threshold may be established as 0.5°. Thus, CAS system may compare the current orientation angle, $\theta_T$, with the threshold angle of 0.5°. If the tool axis 403 is not within 0.5° of the target axis 401 (i.e., $\theta_T$<0.5°) (Step 745: No), the process may revert back to step 725.

If, on the other hand, the current tool orientation angle, $\theta_T$, is within the threshold angle (Step 745: Yes), force system of CAS system 200 may engage orientation "hold" forces (Step 750). Tool "hold" forces may be haptic forces that are designed to constrain or lock cutting tool 103 in the current orientation. Accordingly, these hold forces prevent, constrain, or inhibit the tool from being rotated away from the current tool orientation angle, $\theta_T$.

Once tool axis 403 has been properly aligned to within a threshold orientation angle of target axis 401, CAS system 200 may be configured to release or remove haptic forces associated with intermediate tool stop haptic plane 420 (Step 755). As such, reference point 103a associated with cutting tool 103 may be allowed to advance past intermediate tool stop haptic plane 420 toward the bone engagement surface, and proceed to the planned target end point 402.

In addition to guiding tool axis 403 of cutting tool 103 to a target orientation (e.g., parallel with target axis 401), CAS system 200 may also be configured to use haptic force control to guide a tool reference point 103a to target axis 401. Specifically, as illustrated in FIG. 7, after CAS system 200 determines that tool reference point 103 is within the volume defined by virtual haptic geometry 400 (Step 720: Yes), CAS system may determine the position of tool reference point 103a (e.g., tool control point) (Step 760). As explained, tool reference point 103a may be registered in the virtual coordinate space of CAS system 200. As such, the relative position of reference point 103a within surgical environment 100 may be tracked by tracking system 201 of CAS system 200. Thus, tracking software associated with CAS system 200 may monitor and, if so configured, display the relative position of reference point 103a within the virtual coordinate space.

Once the current position of tool reference point 103a has been determined, CAS system 200 may determine whether reference point 103a is within the haptic volume defined by virtual haptic boundary 400 (Step 765). As explained, tracking system 201 of CAS system 200 may be configured to track the registered position of tool reference point 103a within surgical environment 100. Similarly, CAS system 200 may be configured to monitor the location, position, and orientation of boundary surfaces 404 of virtual haptic boundary 300. As such, tracking software associated with CAS system 200 may compare the position of reference point 103a of cutting tool 103 with the position of the boundary surfaces 404 associated with virtual haptic boundary. If reference point 103a is not within the haptic volume associated with the virtual haptic boundary 400 (Step 765: No), the process may revert back to step 760, where CAS system 200 continues to monitor position of tool reference point 103a.

If, on the other hand, reference point 103a is within the haptic volume defined by virtual haptic boundary 400 (Step 765: Yes), CAS system 200 may enable haptic forces associated with virtual haptic boundary 400 (Step 770). As explained in connection with the exemplary embodiments, haptic forces are conditionally applied to constrain movement of cutting tool 103 upon detection of an interaction between cutting tool 103 and boundary surface 404 of virtual haptic geometry 400, in order to prevent undesired movement or positioning of cutting tool 103 outside of virtual haptic geometry 400.

Once the haptic forces associated with the haptic volume have been activated, CAS system 200 may determine whether tool reference point 103a is attempting to "break" through the boundary surface(s) 404 of virtual haptic geometry 400 (Step 775). According to one embodiment, this involves tracking the position of tool reference point 103a within the volume defined by virtual haptic geometry 400. The tracked position of reference point 103a may be compared with the position of boundary surface 404. Tracking system 201 of CAS system 200 may be configured to determine when the position of reference point 103a interferes, intersects, or otherwise overlaps with boundary surface 404. As the position of reference point 103a interferes with the position of boundary surface 404, CAS system 200 may be configured to detect that reference point 103a is trying to "break" through the haptic boundary defined by virtual haptic geometry 400.

In situations in which tool reference point 103a is not trying to break through boundary surface 404 corresponding to virtual haptic geometry 200 (Step 775: No), the process may revert back to step 760, where CAS system 200 continues to monitor position of tool reference point 103a. If, however, tracking system 201 associated with CAS system 200 determines that reference point 103a is trying to "break" through boundary surface 404 associated with virtual haptic geometry 400 (Step 775: Yes), force system of CAS system 200 may be configured to apply corresponding haptic forces to constrain the tool center point within the haptic volume (Step 780). According to one embodiment, CAS system 200 is configured as an impedance-type haptic system, whereby haptic forces are designed to simulate a mechanical impedance based on the position of reference point 103a relative to boundary surface 404 of virtual haptic geometry 400. It is contemplated, however, that, although the exemplary embodiments are described with respect to CAS system 200 being embodied as a impedance-type haptic system, that certain processes and methods consistent with the disclosed embodiments are compatible with admittance-type haptic force control systems.

It is also contemplated that virtual haptic geometry 400 may be configured to constrain movement of the position and orientation of cutting tool 103 while reference point 103a is located within the volume defined by virtual haptic geometry 400. It is contemplated, however, that the virtual haptic geometry 400 (and/or haptic forces associated therewith) may be deactivated, for example, by removing cutting tool 103 from the haptic volume associated with virtual haptic geometry 400 in a predetermined manner, such as by extracting the tip of cutting tool 103 from the top of virtual haptic geometry 400.

FIG. 8 illustrates an exemplary screen shot 800 associated with a graphical user interface of CAS system 200. As illustrated in FIG. 8, CAS system 200 may provide a graphical user interface that displays certain aspects associated with surgical environment 100 on one or more displays 203a, 203b. According to an exemplary embodiment, the graphical user interface may provide a display of the virtual haptic geometry 400 relative to one or more features associated with the surgical environment 100, such as femur 101. As such, CAS system 200 may be adapted to provide a graphical display that, in addition to the haptic guidance, can assist the surgeon in guiding cutting tool 103 toward a target approach orientation (target axis 401) and, ultimately, a target point 402. During use, the graphical user interface may also track tool axis 403 and tool reference point 103a of cutting tool 103 relative to the other displayed aspects of surgical environment 100. Furthermore, graphical user interface of CAS system 200 may also display any modifications of virtual haptic geometry 400 that result from the disclosed methods for guiding cutting tool 103.

It should be noted that, although virtual haptic geometry is illustrated and described in the exemplary embodiments as being a substantially funnel-shaped boundary for use in guiding a surgical drill or burr to a target point, the presently disclosed embodiments are applicable for generating virtual haptic boundaries having different revolute shapes for use with other types of tools. For example, the presently disclosed embodiments contemplate generating a collapsible virtual haptic geometry having a substantially "Y"-shaped cross section having a substantially "V"-shaped upper section that converges to a substantially planar lower section for guiding a planar or sagittal saw toward a desired orientation for executing a planar cut on a bone. Consequently, it is contemplated that the methods described herein may be employed in virtually any environment where it may be advantageous to guide a surgical tool to a predetermined orientation for approaching a target tool operation site.

The presently disclosed systems and methods provide a solution that enables a computer-assisted surgical system to quickly, efficiently, and accurately guide a surgical tool to a target approach orientation and, ultimately, to a target point. More specifically, the systems and methods described herein implement a collapsible virtual haptic geometry that updates the location of haptic forces in response to real-time modifications to the position cutting tool 103 to discourage or constrain the surgeon from moving the cutting tool 103 to a position and/or orientation that does not converge toward a desired orientation.

CAS systems 200 configured in accordance with the presently disclosed embodiments may have several advantages. For example, by providing a collapsible virtual haptic geometry that only allows orientation of the surgical tool to be modified in a manner that converges on a target axis, the presently disclosed CAS systems 200 may significantly decrease the amount of time required to properly orient cutting tool 103 to reach its desired target point. This may ultimately decrease the amount of tinge required to perform the required surgical tasks, particularly when compared with conventional techniques that require the surgeon to "find" the proper orientation through trial-and-error searching.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, micro-processors, and the like. Additionally, although disclosed aspects are described as being stored in a memory, one skilled in the art will appreciate that these aspects can also be stored on other types of computer-readable storage devices, such as secondary storage devices, like hard disks, floppy disks, a CD-ROM, USB media, DVD, or other forms of RAM or ROM.

It will be apparent to those skilled in the art that various modifications and variations can be made to the disclosed systems and associated methods for guiding a surgical instrument to a target orientation and/or position. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:
1. A system comprising:
a surgical device for performing at least one task associated with a surgical procedure; and
a processor operatively coupled to the surgical device and configured to:
determine a current orientation angle of an instrument axis of a surgical tool based on an orientation of a target axis when the instrument axis is not aligned with the target axis;
control the surgical device to apply a force based on the current orientation angle of the instrument axis, the force configured to constrain the instrument axis from being rotated to an angle greater than the current orientation angle.

2. The system of claim 1, wherein the processor is configured to:
establish a virtual boundary, the processor configured to control the surgical device to apply the force to constrain the instrument axis within the virtual boundary; and
modify the virtual boundary to collapse the virtual boundary as the instrument axis is brought into alignment with the target axis.

3. The system of claim 1, wherein the processor is configured to determine the current orientation angle of the instrument axis based on an orientation of the target axis by:
determining whether the instrument axis is coplanar with the target axis; and
if the instrument axis is coplanar with the target axis, measuring an orientation of the instrument axis relative to the target axis; and
if the instrument axis is not coplanar with the target axis:
identifying a line parallel with the target axis and coplanar to the instrument axis; and
measuring an orientation of the instrument axis relative to the identified line.

4. The system of claim 3, wherein the line parallel with the target axis is normal to a plane that is normal to the target axis.

5. The system of claim 1, wherein the processor is further configured to:
establish a virtual volume based on the target axis, wherein the virtual volume defines a boundary at which the force is applied to the surgical tool by the surgical device;
determine a position of a reference point of the surgical tool;
detect a decrease in the current orientation angle of the instrument axis; and
decrease the virtual volume in response to a determination that the reference point is within the virtual volume and the decrease in the current orientation angle of the instrument axis.

6. The system of claim 5, wherein the processor is configured to decrease the virtual volume by decreasing a distance of the boundary of the virtual volume from the target axis.

7. The system of claim 6, wherein the virtual volume is funnel-shaped and the processor is further configured to decrease the distance of the boundary of the virtual volume from the target axis by decreasing a base radius of the virtual volume.

8. The system of claim 6, wherein at least a portion of the virtual volume is substantially cone-shaped, and the processor is further configured to decrease the distance of the boundary of the virtual volume from the target axis by decreasing a boundary angle of the virtual volume.

9. The system of claim 5, further wherein the processor is further configured to determine a distance between the reference point and the target axis and control the surgical device to provide a force that constrains the reference point of the surgical tool from being moved to increase the distance between the reference point of the surgical tool and the target axis.

10. The system of claim 9, wherein the processor is further configured to:

determine whether the distance between the reference point and the target axis is less than a threshold distance; and
in response to a determination that the distance between the reference point and the target axis is less than a threshold distance, control the surgical device to apply a second force configured to urge the reference point to a position along the target axis.

11. The system of claim 1, wherein the force comprises haptic feedback.

12. A system, comprising:
a surgical device;
an instrument coupled to the surgical device and defining an instrument axis;
a processor operatively coupled to the surgical device and configured to:
determine a current orientation angle of an instrument axis based on an orientation of a target axis when the instrument axis is not aligned with the target axis;
establish a virtual boundary;
control the surgical device to apply a force to constrain the instrument axis within the virtual boundary; and
collapse the virtual boundary as the instrument axis is brought into alignment with the target axis.

13. The system of claim 12, wherein the processor is configured to determine the current orientation angle of the instrument axis based on an orientation of the target axis by:
determining whether the instrument axis is coplanar with the target axis; and
if the instrument axis is coplanar with the target axis, measuring an orientation of the instrument axis relative to the target axis; and
if the instrument axis is not coplanar with the target axis:
identifying a line parallel with the target axis and coplanar to the instrument axis; and
measuring an orientation of the instrument axis relative to the identified line.

14. The system of claim 12, wherein the virtual boundary defines a virtual volume and the processor is configured to:
detect a decrease in the current orientation angle of the instrument axis; and
reduce the virtual volume in response to a combination of a determination that a reference point of the instrument is within the virtual volume and the decrease in the current orientation angle of the instrument axis.

15. The system of claim 12, wherein the processor is configured to:
detect a decrease in the current orientation angle of the instrument axis; and
in response to the decrease in the current orientation angle of the instrument axis, reduce a distance between the virtual boundary and the target axis.

16. The system of claim 15, wherein the virtual boundary comprises a funnel shape and the processor is configured to reduce the distance of virtual boundary from the target axis by decreasing a base radius of the funnel shape.

17. The system of claim 15, wherein the virtual boundary comprises a cone shape and the processor is configured to reduce the distance of the virtual boundary from the target axis by decreasing a boundary angle of the cone shape.

18. The system of claim 15, comprising a tracking system configured to collect data indicative of a pose of the instrument and provide the data to the processor.

19. The system of claim 12, wherein the processor is configured to:
detect a translation of the instrument axis towards the target axis; and in response to the translation of the instrument axis towards the target axis, reduce a distance of the virtual boundary from the target axis.

20. The system of claim 12, wherein the processor is further configured to:
  determine whether a deviation of the instrument axis from the target axis is less than a threshold; and
  in response to a determination that the deviation of the instrument axis from the target axis is less than the threshold; control the surgical device to apply a second force configured to urge the instrument axis toward the target axis.

\* \* \* \* \*